US006781276B1

(12) United States Patent
Stiesdal et al.

(10) Patent No.: US 6,781,276 B1
(45) Date of Patent: Aug. 24, 2004

(54) GENERATOR FOR A WINDMILL, STATOR MODULE FOR USE IN SUCH A GENERATOR AND USE OF SUCH A GENERATOR

(75) Inventors: Henrik Stiesdal, Brande (DK); Peter Rasmussen, Svendborg (DK)

(73) Assignee: Bonus Enegy A/S, Brande (DK)

( * ) Notice: Subject to any disclaimer, the term of this patent is extended or adjusted under 35 U.S.C. 154(b) by 0 days.

(21) Appl. No.: 09/937,711

(22) PCT Filed: Mar. 31, 2000

(86) PCT No.: PCT/DK00/00162

§ 371 (c)(1),
(2), (4) Date: Oct. 1, 2001

(87) PCT Pub. No.: WO00/60719

PCT Pub. Date: Oct. 12, 2000

(30) Foreign Application Priority Data

Mar. 31, 1999 (DK) .......................................... 1999 00451
Nov. 17, 1999 (DK) .......................................... 1999 01655

(51) Int. Cl.[7] .............................................. H02K 1/12
(52) U.S. Cl. ....................... 310/254; 310/258; 310/259; 290/44
(58) Field of Search ................................. 310/254, 258, 310/257, 88, 259, 218, 217; 290/42, 44

(56) References Cited

U.S. PATENT DOCUMENTS

| | | | | | |
|---|---|---|---|---|---|
| 2,774,000 | A | * | 12/1956 | Ross ........................... | 310/216 |
| 4,080,724 | A | * | 3/1978 | Gillette ......................... | 29/598 |
| 4,866,321 | A | * | 9/1989 | Blanchard et al. .......... | 310/112 |
| 5,212,419 | A | * | 5/1993 | Fisher et al. ................. | 310/254 |
| 5,315,159 | A | * | 5/1994 | Gribnau ....................... | 290/55 |
| 5,382,859 | A | * | 1/1995 | Huang et al. ................ | 310/216 |
| 5,418,446 | A | * | 5/1995 | Hallidy ........................ | 322/28 |
| 5,506,453 | A | * | 4/1996 | McCombs .................... | 290/44 |
| 5,619,082 | A | * | 4/1997 | Choi ............................ | 310/88 |
| 5,714,827 | A | * | 2/1998 | Hansson ...................... | 310/254 |
| 5,844,341 | A | * | 12/1998 | Spooner et al. ............. | 310/112 |
| 6,144,130 | A | * | 11/2000 | Kawamura ............. | 310/156.28 |
| 6,321,439 | B1 | * | 11/2001 | Berrong et al. ............... | 29/596 |
| 6,583,530 | B2 | * | 6/2003 | Hsu ........................... | 310/254 |
| 2002/0163272 | A1 | * | 11/2002 | Larsson et al. ............. | 310/180 |
| 2003/0048030 | A1 | * | 3/2003 | Griffith et al. .............. | 310/254 |

FOREIGN PATENT DOCUMENTS

| | | | | | |
|---|---|---|---|---|---|
| JP | 58204746 | * | 11/1983 | ............ | H02K/3/34 |
| JP | 08265995 | * | 3/1995 | ............ | H02K/1/14 |
| JP | 09322439 | * | 12/1997 | ............ | H02K/1/14 |
| JP | 10322942 | * | 12/1998 | ............ | H02K/1/18 |
| JP | 2000139052 | * | 5/2000 | ............ | H02K/3/34 |
| JP | 2000324728 | * | 11/2000 | ............ | H02K/1/14 |
| JP | 2001037135 | * | 2/2001 | ............ | H02K/3/34 |
| JP | 2002218725 | * | 8/2002 | ............ | H02K/29/00 |
| SE | WO98/20595 | * | 5/1998 | ............ | H02K/1/16 |

* cited by examiner

Primary Examiner—Burton S. Mullins
Assistant Examiner—Heba Elkassabgi
(74) Attorney, Agent, or Firm—James Creighton Wray; Meera P. Narasimhan

(57) ABSTRACT

The invention concerns a generator for a windmill. The generator is of the kind being directly coupled to the main shaft of the wind rotor of the windmill. The generator is a stator consisting of a number of stator modules that are individual and which may be installed, repaired and dismantled individually and independently of each other. This implies that it is very easy and thereby cheaper to mount the mill, especially at sea, as the stator for the generator can be transported in smaller units, which also makes it easier to assemble the stator in the tower top section. By sequent repairs and other maintenance of the generator it is not necessary either to use large cranes, but it is sufficient to use smaller hoisting devices that may be handled by one or two persons.

10 Claims, 7 Drawing Sheets

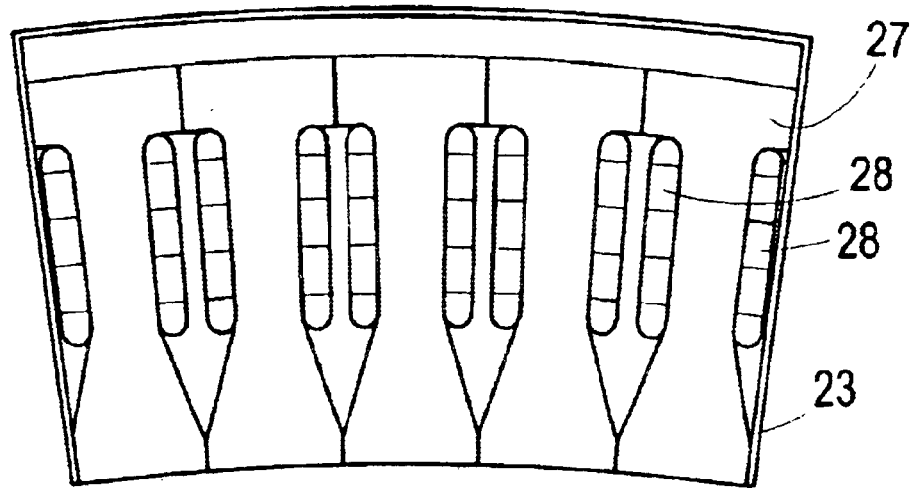
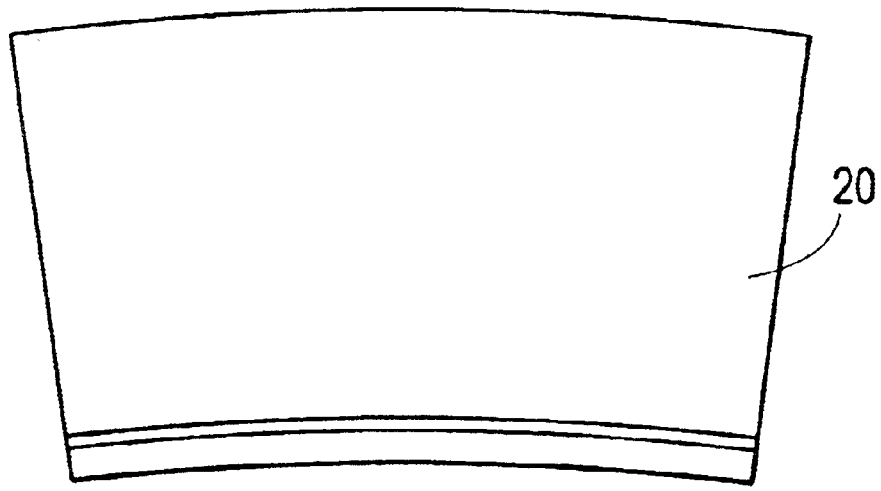
Fig.7

GENERATOR FOR A WINDMILL, STATOR MODULE FOR USE IN SUCH A GENERATOR AND USE OF SUCH A GENERATOR

BACKGROUND OF THE INVENTION

The present invention relates to a generator for a windmill of the kind driven directly by the rotor of the windmill without any gearbox installed between the rotor and the generator wherein at least the stator of the generator is made of modules of which one or more stator modules can be dismantled independently without having to dismantle the entire winding. It is known that it is necessary to insert a speed increasing gearbox between the rotor and the generator of a windmill The rotational speed is of the magnitude 20 rpm for large windmills while a normal 4-pole generator has a synchronous speed of rotation of 1500 rpm. A suitable speed increasing gearbox will thus have a gear ratio of 1:75.

It is known that the speed increasing main gearbox of a windmill constitutes a substantial part of the cost price, and besides that it is a relatively vulnerable main component. In many cases, by possible damages, it will be necessary to dismantle the gearbox for repair. In consideration of the gearbox for a windmill in the 2 MW class having a weight of up to 15 tons and being mounted in a machine disposed on a tower with a height of 60–100m it is obvious that such a replacement may be very costly. The risk of incurring considerable expenses by a possible replacement is multiplied if large windmills are erected at sea Handling of weights of 15 tons or more in 60–100 m height may only be performed with very large float cranes or very large mobile cranes placed on large barges. Working with this kind of equipment at the open sea can only be done under good weather conditions. Therefore, there may be periods of several months during the winter where it is not possible to replace a damaged gearbox.

The generator itself is also a heavy main component, typically with a weight of 5 tons by 2 MW rated output. As with the gearbox it cannot be avoided that there will be a certain risk of breakdown of the generator. The conditions by replacing this are just as adverse as for the gearbox.

It is also known that there are gearless transmission systems for windmills where gearbox and generator are substituted by a slowly turning, multipolar generator. Such a directly driven generator can be made as a synchronous generator with winded rotor or with permanent magnets, or it can be designed as alternative types of generators. Common to directly driven, multipolar generators is that their dimensions are great. The air gap diameter by 2 MW rated output may e.g. be of the magnitude 5 m by an embodiment with winded rotor, and a little less by an embodiment with permanently magnetised rotor.

By a directly driven, multipolar generator the gearbox becomes superfluous. Usually, it will be necessary to insert a frequency converter between the generator and the network since it is difficult to achieve a pole number corresponding to the 50 Hz mains frequency by nominal rpm. Hence multipolar generators normally generate alternating current with a somewhat lower frequency, e.g. 20 Hz, whereby the number of poles may be reduced to ⅔, and more space for the coil windings is provided. Even though the frequency converter constitutes increased complexity in relation to a generator system where the generator is coupled directly to the network, it may be appreciated that the reduction in complexity by elimination of the main gearbox more than offsets this.

A substantial drawback by a directly driven multipolar generator are the physical dimensions. By an air gap diameter of 5 m, the outer diameter becomes in the magnitude of 6 m and the dead load becomes about the dead load the replaced components, gearbox and normal generator, i.e. 20 tons or more. The large outer diameter makes transport difficult, and the dead load does not reduce the problem with replacement for repair by possible breakdowns.

A further difficulty arises in the normal configurations with multipolar generators where the generator is placed between the rotor and the tower in order to yield a compact machine construction. In addition, here it will be necessary to dismantle the whole rotor by eventual dismantling of the generator.

From WO-A1-98/20595 a stator assembled from modules is known, where the stator windings on each module can be premade, and the entire winding can thereafter be assembled on site. This construction makes transport to the site of erection easier. This construction requires a stator housing as such, and this stator housing requires a diameter which is substantially larger than the air gap diameter.

From U.S. Pat. No. 4,594,552 another generator having a stator built from modules is known, which modules can be dismantled without the entire winding being dismantled This construction, however, also requires a stator housing as such, and that the stator housing has a diameter substantially larger than the air gap diameter.

There is known an embodiment of a directly driven generator, U.S. Pat. No. 5,844,341, where the stator of the generator is made with modules which largely constitute individual polar pairs and which are disposed on support arms outside the poles. The advantage of this construction is that a damaged part of the generator may be replaced without taking down the whole generator. The drawback by this configuration is, however, that the electromechanical properties in this form of modular construction with single polar pairs separated by air gaps may be disadvantageous, and that possible dismantling of a single stator module can involve that the whole generator has to be opened in situ implying risk of humidity, dirt etc., and that it may be cumbersome if the stator module has to be taken out in a disadvantageous direction.

Another design of a directly driven generator is known, U.S. Pat. No. 4,866,321, where an axial generator has a stator designed with modules each containing a single pole winded around a coil and installed in an arrangement where the coil may be drawn radially out from the stator. The advantage of this construction is, as with the previous, that a damaged pole in the generator may be replaced without the whole generator to be taken down. As a consequence of the mechanical construction it is likely that the electromechanical properties will be better than in the above arrangement The draw-back is, however, that possible dismantling of a single stator module can involve that the whole generator has to be opened in situ implying risk of humidity, dirt etc., and that it may be cumbersome if the stator module has to be taken out in a disadvantageous direction.

SUMMARY OF THE INVENTION

It is the purpose of the present invention to provide a generator of the kind described above, wherein the advantages of a directly driven, multipolar generator are preserved, and where the drawbacks connected with known generators are relieved such that it is possible not to have a stator housing as such whereby the diameter of the construction can be limited, and be made with a size substantially corresponding to the air gap diameter.

This purpose is achieved according to the present invention with a generator which is peculiar in that each single stator module is individually contained in an enclosure with a degree of sealing substantially corresponding to the degree of sealing which is desired in the finished generator, and that a given number of juxtaposed enclosures abutting on each other form a closed ring of stator modules.

By designing the generator according to the invention a number of advantages are attained as compared with the prior art The advantages of a directly driven, multipolar generator as compared with more conventional transmission systems with gearbox and standard generator are maintained in a generator according to the invention By designing the electrically active part of the generator stator as modules, each having the necessary degree of sealing (typically there is desired sealing corresponding to IP54 in accordance with IEC 529), a stator housing as such is not necessary, the structural part of the stator housing adapted for mounting of the modules may be designed with an outer diameter substantially as the air gap diameter. Hereby the outer diameter of the part of the stator normally being installed when transporting the windmill to the erection site is reduced to the minimum determined by the air gap. Concerning the transport, there is a substantial advantage in having the least possible outer diameter. The winding modules of the stator then have to be retrofitted at the erection site.

By making the winding as modules, the space requirements and the complexity in the winding are reduced considerably. The stator modules may be performed in serial production, and the single modules may be finished with sealing, terminal box etc. under convenient conditions. Therefore, the risk becomes much less for winding damages caused by handling under difficult access conditions in a large construction.

A special embodiment of a stator module according to the invention is characterised in that the stator module is intended for constituting a part of a complete stator, and that the stator module is contained in an enclosure with tightness corresponding to a given desired degree of enclosure.

By making the stator modules with the necessary tightness so that they may be installed and dismantled in situ there is achieved a very essential advantage by possible damages. Damages on a generator winding arise normally by an initial flashover at one locality, e.g. due to accidental isolation damages, humidity or the like. Because of the great amounts of energy released by a burning off, the damage however, typically causes more general effects on the whole winding in a standard generator. Large parts of the winding may be damaged by melting, by other thermal effects and by sooting up. In the modular construction generator however, the damage is usually limited just to the module in which the initial flashover occurred. Thus it is not necessary that the whole winding is dismantled as the repair may be limited to the module(s) concerned.

The segmented construction of the generator gives the possibility of utilising particularly advantageous material properties normally not available by rotating electric machines. The fact is that iron can be made with directional magnetic properties. This kind of field oriented iron is used in transformers and is therefore normally denoted transformer sheet metal. On a normal rotating machine where sheet metal for stator and rotor is punched in one piece, transformer sheet metal cannot be used as the magnet field lines will have every direction about the rotor axis. The advantage of the good magnetic properties in the most advantageous field direction is therefore more than offset by corresponding bad magnetic properties perpendicular to the most advantageous field direction. Therefore, on rotating machines so-called motor sheet metal is used, which does not have directional magnetic properties. The iron losses are therefore somewhat greater in rotating machines than in transformers with corresponding variations in flux.

On the segmented generator, however, the situation is otherwise than on normal rotating machines. By making the generator with six or more stator modules it may be achieved that the magnet field lines within each segment will not deviate much more than 10 degrees from the most advantageous direction in the iron. The use of transformer sheet metal therefore becomes relevant and thereby there is achieved possibility of a considerable reduction of the magnetising losses as compared with the losses when using generator sheet metal, Furthermore, a better magnetic conductivity is achieved whereby higher induction and field strength in the air gap is achieved with consequently greater magnetic power and torque.

By the handling itself essential advantages are also achieved. Each single module will have a weight much less than the complete generator, and also much less than the weight of a normal gearbox or a normal generator. By a directly driven multipolar generator with a weight of 20 tons, the modules may conveniently be made in a number so that each has a weight of 500 kg. By a weight of this magnitude the modules may be replaced singularly by a few fitters by means of a small crane which advantageously may be built into the cabin of a windmill.

The advantage compared with prior art is especially of importance where large windmills are erected at sea. The very large floating cranes or very large mobile cranes on large barges necessary for repair works on known transmissions systems, whether these are conventional with gearbox and standard generator, or with directly driven, multipolar generator, may be completely avoided. The only condition for repair is that it is possible to get service personnel on the mill. Replaced generator modules may be lowered by a small built-in crane, and they may be sailed to and from the windmill on a normal service boat. A number of generator modules may even be stored in the mill top as spare parts, whereby lowering and sea transport may be postponed until periods with favourable weather conditions.

By making the generator in a shaft mounted version where the torque is absorbed at some specific points by moment supports, there may be achieved the advantage that the stator of the generator may be turned to the most optimal position by repair works. Installing and dismantling modules may therefore occur at one definite position irrespectively of where each module is disposed on the generator when the generator is in its normal operative position. For example the stator of the generator may be turned so that the module to be replaced turns downward and therefore may immediately be lowered through a hatch at the bottom of the windmill cabin.

DESCRIPTION OF THE DRAWING

The invention is described more closely in the following as reference is made to the drawing, where:

A BRIEF DESCRIPTION OF THE DRAWINGS

Figure 1:
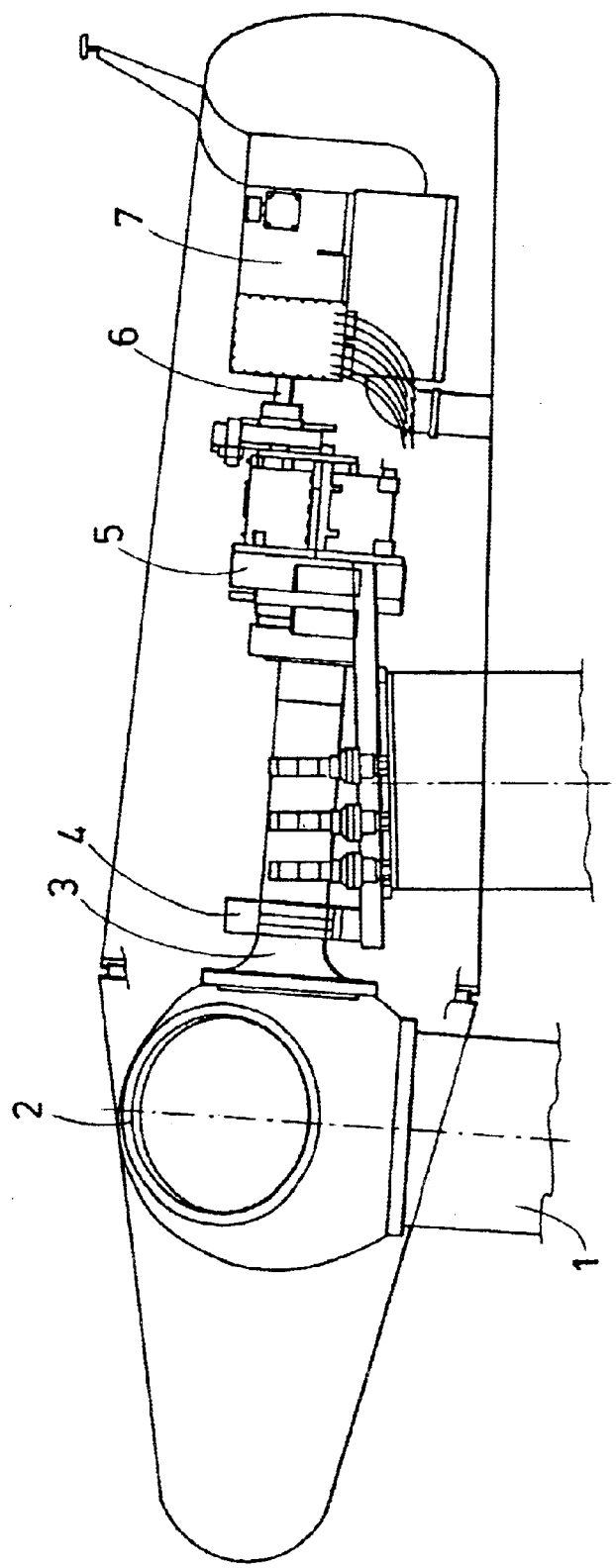
Figure 2:
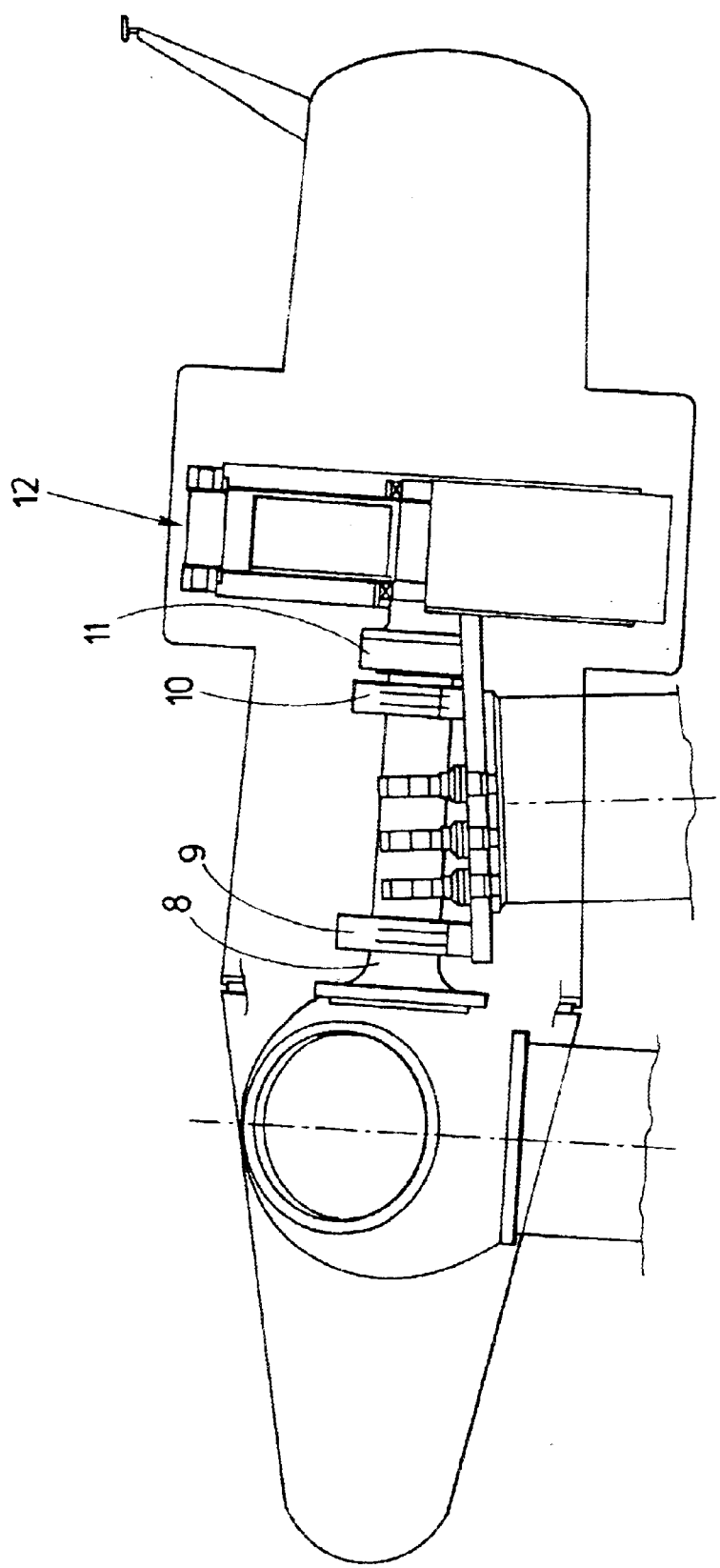
Figure 3:
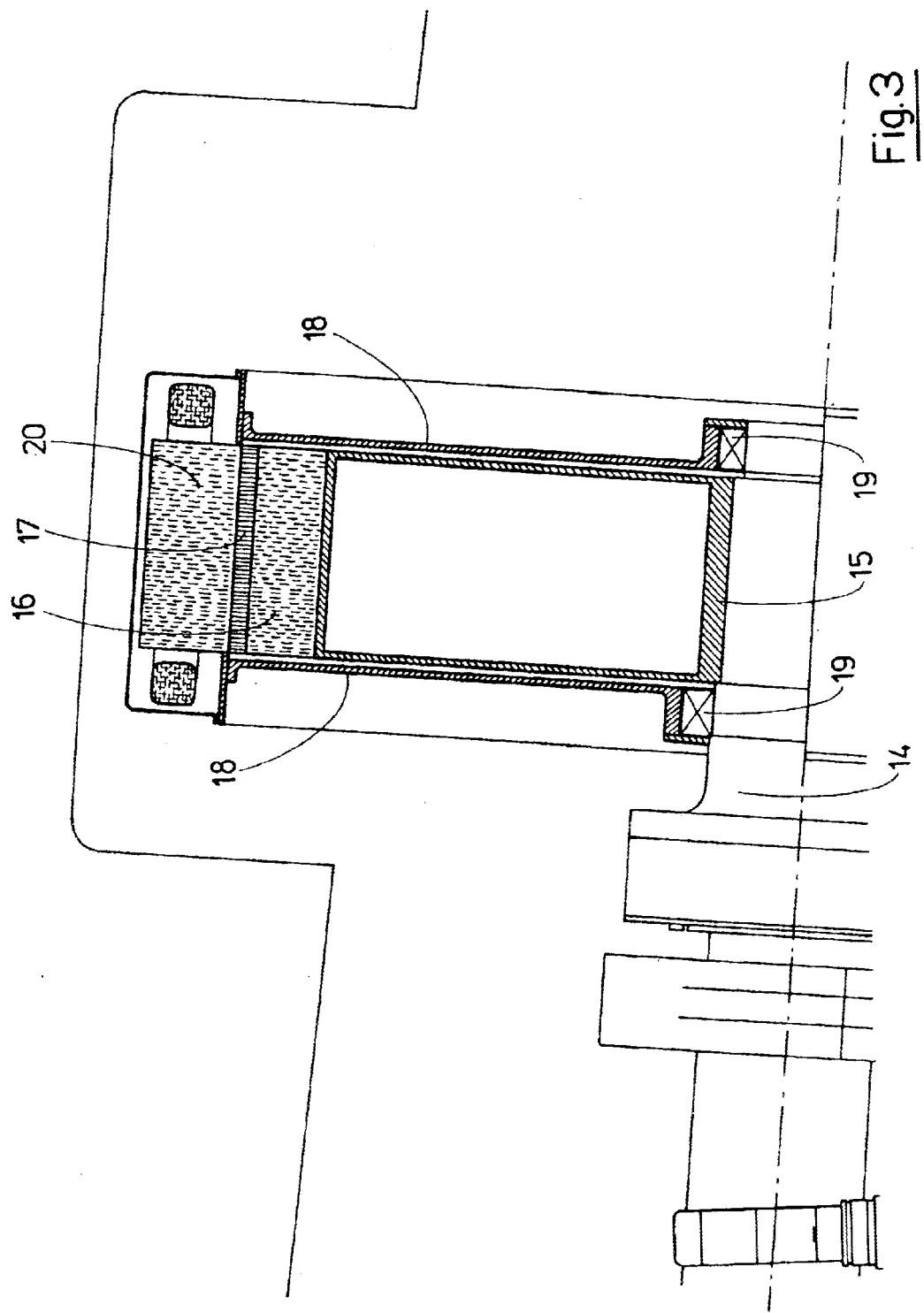
Figure 4:
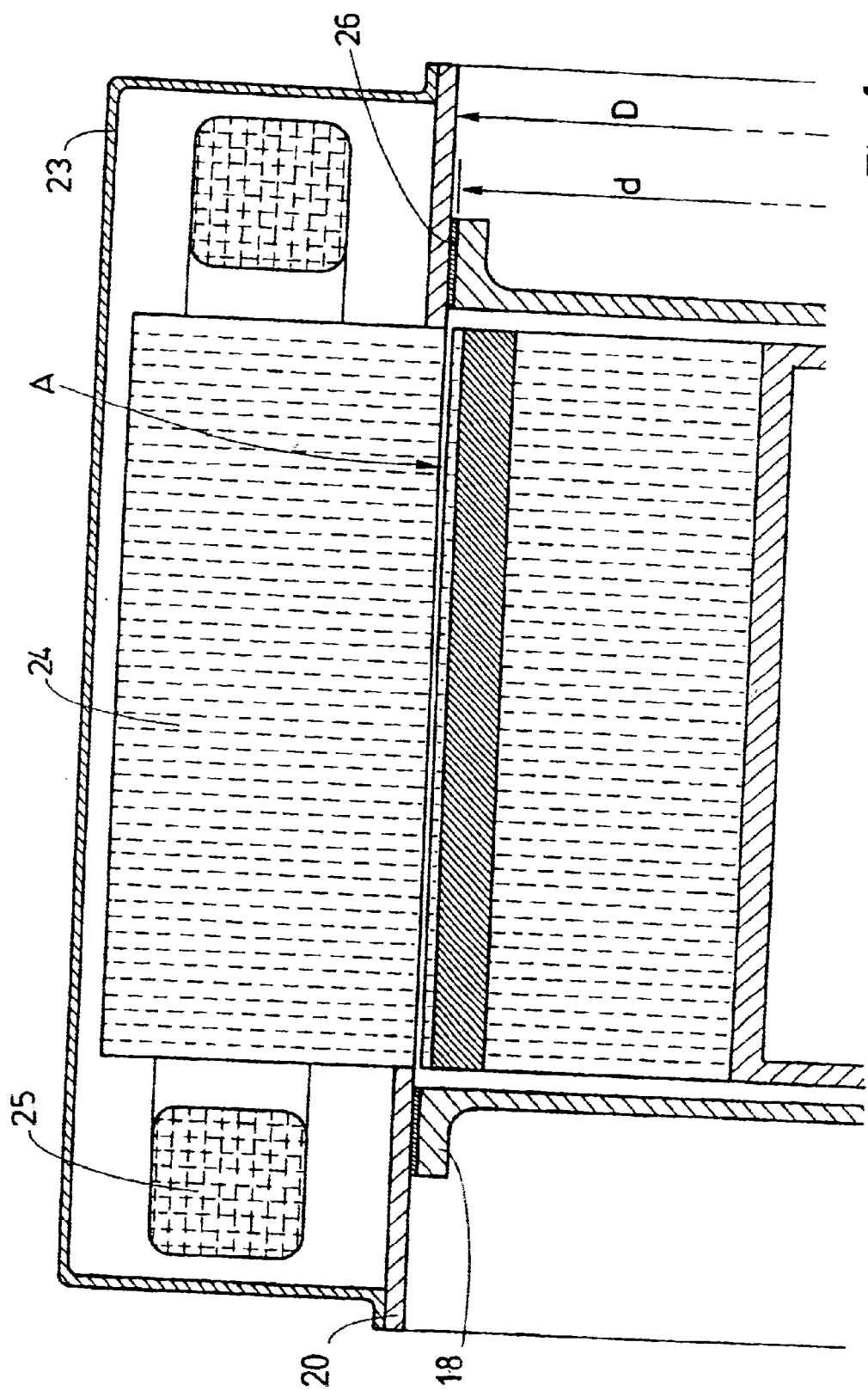
Figure 5:
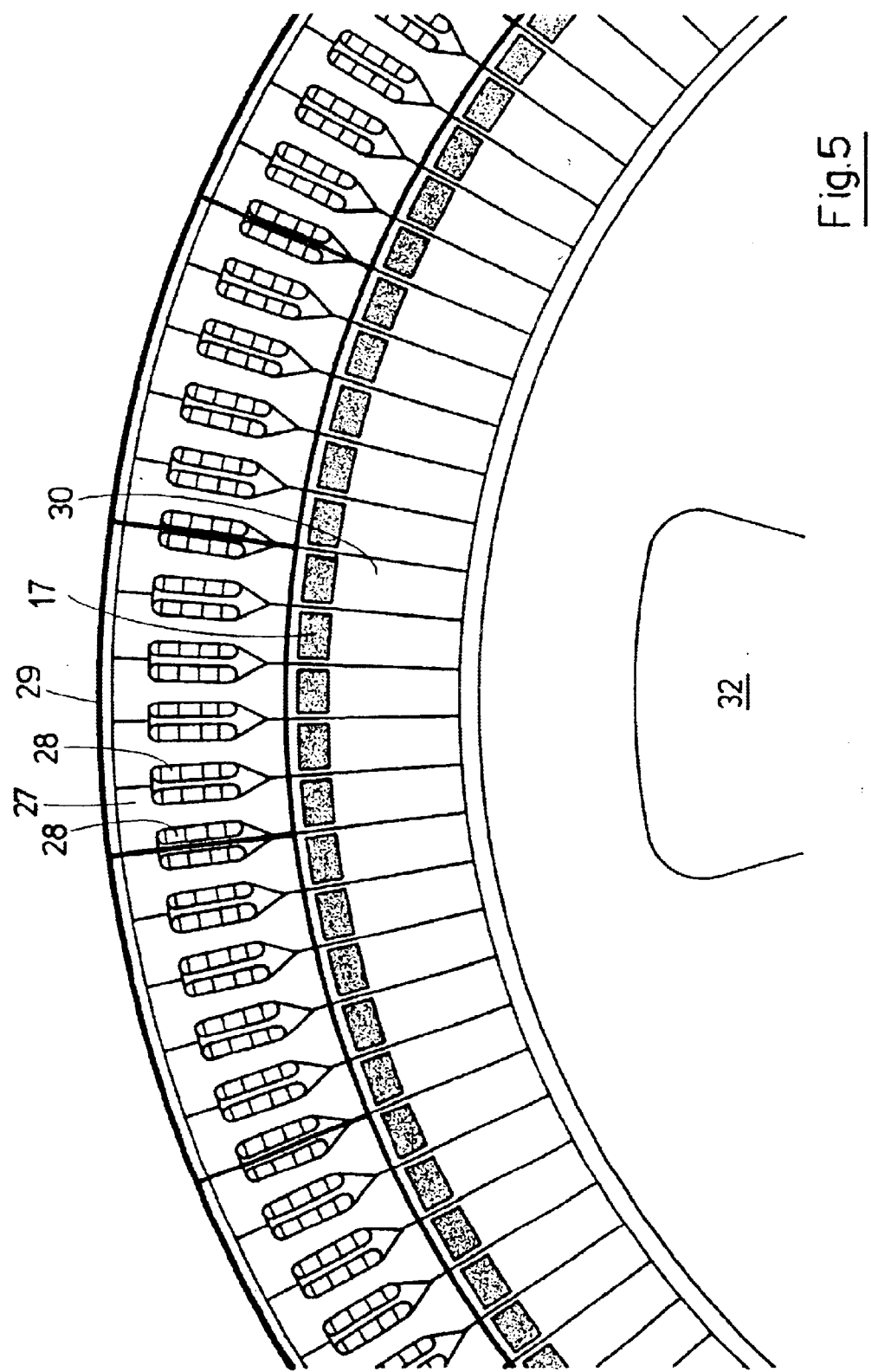
Figure 6:
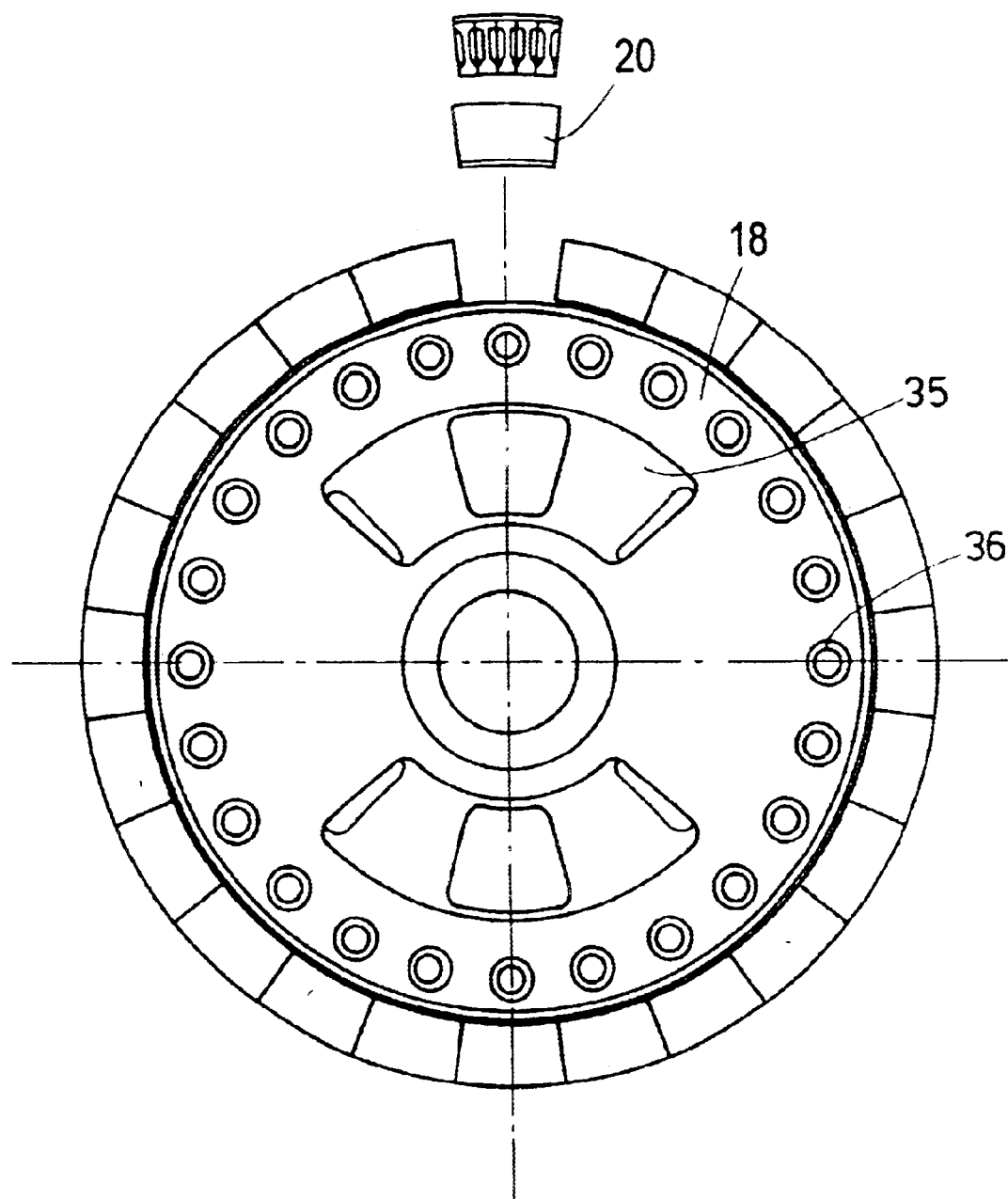

FIG. 1 is an illustration of a prior art kind of tower top section of a windmill, FIG. 2 is an illustration of an embodiment of a tower top section of a windmill with a generator according to the invention, FIG. 3 is a detailed illustration of a generator according to the invention as seen perpendicularly to an axis of the generator, FIG. 4 is a further detailed illustration of a generator according to the invention, FIG. 5 is a detailed illustration of a generator according to the invention viewed in parallel with an axis of the generator, FIG. 6 is a second detailed illustration of a generator according to the invention, and FIG. 7 is an illustration of an embodiment of a stator module according to the invention.

A DETAILED DESCRIPTION OF THE PREFERRED EMBODIMENTS

In, the design shown in the figures, the generator is with 120 poles in 24 stator modules. The generator is permanently magnetised. Other embodiments, including such with brushless as well as slipring magnetisation of a winded rotor, are also suitable. Here it may be relevant to design a winded rotor so that the rotor also has modules. Such a special embodiment is not described any further here.

FIG. 1 shows a prior art windmill in normal design with gearbox and standard generator. The wings 1 of the rotor are mounted on the mill hub 2 which is fastened to the main shaft 3. The main shaft is supported by a main bearing 4 at the front and by the gearbox 5 at the rear. The gearbox is connected to the generator 7 with an elastic coupling 6.

FIG. 2 shows a windmill designed according to the invention. The main shaft 8 is supported by a front main bearing 9 and a rear main bearing 10. The main bearing has a split bushing 11 as flange at the rear. The generator 12 has a shaft 14 (see FIG. 3) which is supported by the flange 11 of the main shaft.

FIG. 3 shows an enlarged longitudinal section of the generator. The generator shaft 14 supports the structure IS of the rotor which at its periphery has the rotor sheet metal 16 and the permanent magnets 17. The stator housing 18 is supported by the generator bearings 19 and has the stator modules 20 at its periphery.

FIG. 4 shows more enlarged a-longitudinal section of the stator. The stator housing 18 is connected to the stator module 20 by a screw bolt connection (not shown). The stator module has an enclosure 23 around the stator sheet metal 24 and the stator winding 25. In the shown version, the generator is made with a stator housing having an outer diameter d which is exactly the same as an outer diameter of the rotor. The stator module is thus installed so that the stator module forms an inner diameter D which is greater than the outer diameter d of the rotor and of the rotor housing. An air gap A may easily be adjusted, e.g. by means of adjusting means, in the embodiment shown by means of shims 26, at the joint between stator housing and stator module, and possible dimensional deviations in the stator module may thereby be compensated for.

FIG. 5 shows in part a cross-section of the stator. The single pole 27 has a winding 28 and is protected by the enclosure 29. The single rotor pole 30 has a permanent magnet 17. In the rotor structure, manholes 32 are cut out for convenient passage of the generator.

FIG. 6 shows the complete generator as seen from the main shaft side. One of the stator modules 20 is shown dismantled. The other stator modules are at their respective places on the stator housing 18. Manholes 35 ensure the possibility of going through irrespectively of the position of the rotor. Fittings for torque supports 36 are provided with the same number as the stator modules whereby the stator of the generator may be fastened for vertical lowering of each single module.

The electric connection between the stator modules and is not shown on the Figure. It may e.g. be established in the way that there is mounted one central terminal box on the stator housing, and that from a terminal box on each stator module there is drawn an isolated three-phase cable from the stator module to the central terminal box. Alternatively, there may be established a connection form with three phase rings provided concentrically about the main shaft at one side of the stator housing under suitable covering. Isolated three-phase cables are drawn radially from the three phase rings to the terminal boxes of each of the stator modules, and the main cables transmitting the power to the frequency converter or directly to the network are installed directly on the phase rings.

Irrespectively of the local connections on the generator, it will be convenient to make the main cables from the generator with a certain slack that may absorb the displacements occurring between each stator module and a central terminal box if the stator of the generator is to be turned for each replacement of one or more stator modules. The slack may possibly be reduced for the stator to be capable of being turned only a half turn clockwise or counterclockwise depending on which side of a vertical plane the stator module to be replaced is situated.

FIG. 7 shows a stator module in cross-section and as end view. The pole 27 has its winding 28 and is protected by an enclosure 23. The assembled module 20 appears completely enclosed.

What is claimed is:

1. Generator, preferably for a windmill and especially of the kind driven directly by the rotor of the windmill without any gearbox (5) installed between the rotor and the generator, wherein at least the stator of the generator (12) is made with at least two modules (20) which are fully enclosed and sealed, and that these at least two modules (20) may be mounted and dismantled independently of each other one or more at a time without dismantling the entire winding (25), characterised in that each single stator module (20) is individually contained in an enclosure (23) with a degree of sealing substantially corresponding to the degree of sealing which is desired in the finished generator (12), and that a given number of juxtaposed enclosures (23) abutting on each other form a closed ring of stator modules (20), and wherein the width of the air gap (A) between the rotor and the stator may be adjusted individually for each stator module (20) and independently of each other by suitable adjusting shims (26), by adjusting a distance between an outer periphery (d) of the stator structure and an inner periphery (D) of a given stator module (20).

2. Generator according to claim 1, characterised in that each single stator module (20), when they are installed in a stator, together form a closed ring of stator modules having a diameter which does not substantially exceed the diameter of the air gap of the generator.

3. Generator according to claim 1, characterised in that each single stator module (20) may be displaced radially on the stator structure with the purpose of adjusting the air gap (A).

4. Generator according to claim 1, characterised in that the magnetic circuit in each single stator module is completely or substantially provided by iron having directional magnetic properties.

5. Generator according to claim 1, characterised in that the generator (12) is mounted on a shaft (14), and the stator during mounting and repair work may be turned in relation to the main shaft (8) of the windmill without this requiring substantial dismantling besides the moment support of the generator.

6. Generator according to claim 1, characterised in that the generator (12) during mounting and repair works may be turned in relation to a main shaft (8) of a windmill, in such a way that each single stator module (20) essentially may be lowered vertically to the ground or sea surface.

7. Generator according to claim 1, characterised in that the stator comprises between 2 and 48 modules (20), preferably 24 modules.

8. Generator according to claim 1, characterised in that the juxtaposed enclosures (23) have an inner surface facing inward toward the rotor (15) and forming the inner periphery (D) for the stator, that the inner periphery (D) of the stator is circular, that the rotor has an outer periphery (d) which is also circular, and that the air gap (A) between the outer periphery (D) of the rotor and the inner periphery (d) of the stator substantially have a constant width between 2 mm and 10 mm, preferably 5 mm.

9. Stator module for use in a generator according to claim 1, which stator module comprises at least two poles and a number of windings around the poles, characterised in that the stator module is intended for constituting a part of a complete stator, and that the stator module is contained in an enclosure with a degree of sealing corresponding to a given desired degree of enclosure.

10. Use of a generator according to claim 1 in a windmill.

* * * * *

UNITED STATES PATENT AND TRADEMARK OFFICE
CERTIFICATE OF CORRECTION

PATENT NO. : 6,781,276 B1
APPLICATION NO. : 09/937711
DATED : August 24, 2004
INVENTOR(S) : Stiesdal et al.

It is certified that error appears in the above-identified patent and that said Letters Patent is hereby corrected as shown below:

Title Page:

Item (73) Assignee:

"Bonus Enegy A/S" should read --Bonus Energy A/S--.

Signed and Sealed this

Nineteenth Day of February, 2008

JON W. DUDAS
*Director of the United States Patent and Trademark Office*